United States Patent

Kishimoto et al.

Patent Number: 5,985,788
Date of Patent: Nov. 16, 1999

[54] PROCESS FOR MAKING (METH) ACRYLONITRILES

[75] Inventors: Nobuji Kishimoto, Suita; Taizou Matsueda, Osaka, both of Japan

[73] Assignee: Nippon Shokubai Co Ltd, Osaka, Japan

[21] Appl. No.: 08/721,994

[22] PCT Filed: Jan. 22, 1996

[86] PCT No.: PCT/JP96/00097

§ 371 Date: Oct. 7, 1996

§ 102(e) Date: Oct. 7, 1996

[51] Int. Cl.⁶ .......................... B01J 23/00; C07C 253/00
[52] U.S. Cl. .......................... 502/311; 558/323; 558/325
[58] Field of Search .................. 558/323, 325; 502/311

[56] References Cited

FOREIGN PATENT DOCUMENTS 07157462  6/1995  Japan.

*Primary Examiner*—Johann Richter
*Assistant Examiner*—Joseph Murray
*Attorney, Agent, or Firm*—Sherman & Shalloway

[57] ABSTRACT

A process for the preparation of (meth)acrylonitriles following ammoxidation process comprising catalytically oxidizing at least one saturated hydrocarbon selected from the group consisting of propane and isobutane with a mixed gas containing molecular oxygen and ammonia in the presence of a catalyst, is provided, the process being characterized by the use of a catalyst composed of complex oxide which is expressed by the general formula (I) below:

$$Mo_\alpha Sb_\beta W_\gamma O_x \quad (I)$$

(in which $\alpha$, $\beta$ and $\gamma$ denote the number of atoms of Mo, Sb and W, respectively, and when $\alpha$ is 1, $\beta$ is 0.5–10 and $\gamma$ is 0.5–10; and x is a value determined by valence of the existing elements) as supported on a refractory inorganic carrier.

According to this process, the object nitrites can be prepared at high yields with industrial advantages.

6 Claims, No Drawings

PROCESS FOR MAKING (METH) ACRYLONITRILES

This application is a 371 of PCT/JP96/80097 filed Jan. 22, 1996.

TECHNICAL FIELD

This invention relates to a process for making (meth) acrylonitriles by ammoxidation of at least one saturated hydrocarbon selected from the group consisting of propane and isobutane, in which the hydrocarbon is contacted with molecular oxygen and ammonia in the vapor phase.

TECHNOLOGICAL BACKGROUND (Meth)acrylonitriles have been manufactured in large quantities, as the intermediates for a great variety of industrial products represented by synthetic fibers and synthetic resins. As a conventional production process thereof, ammoxidation is generally known, in which olefinic starting materials, i.e., propylene, isobutene, and the like, are contacted with molecular oxygen and ammonia in the vapor phase, in the presence of a catalyst.

Whereas, with the recent rise in olefin price, development of processes for making the various derivatives which have heretofore been manufactured from olefins, using as the starting materials less expensive paraffins, comes to draw attention. As the catalyst systems used for the production of (meth)acrylonitriles from propane or isobutane by "ammoxidation" process, Sb—U oxide catalyst [Japanese Patent Publication (Kokoku) No. 14371/1972], Sb—Sn oxide catalyst (Kokoku No. 28940/1975), V—Sb oxide catalyst [Japanese Laid-open (Kokai) Nos. 33783/1972, 268668/1989, 95439/1990 and 261544/1990], Bi—Mo oxide catalyst (Kokai No. 16887/1973, Kokoku No. 42071/1980, and Kokai No. 157356/1991], V—P oxide catalyst (Kokoku No. 5188/1983), Bi—V oxide catalyst (Kokai No. 295545/1988), etc. are known. Still recently, furthermore, patent applications have been made for V—Sn—Sb—Cu oxide catalyst (Kokai No. 275266/1992), Mo—V—Te—Nb oxide catalyst (Kokai No. 257/1990), Ag—Bi—V—Mo oxide catalyst (Kokai No. 58961/1991), Ga—Bi—Mo or Ta—Bi—Mo oxide catalyst (Kokai No. 58962/1991), Mo—Ta or Mo—Nb oxide catalyst (Kokai No. 213849/1993), etc. Also mixed catalyst systems of a number of above catalyst systems with those having olefin-ammoxidation ability have been proposed (Kokai Nos. 295546/1988, 38051/1989, 17159/1990, 43949/1990, 75347/1990, 111444/1990 and 258065/1990).

Of these processes, those of adding a minor amount of a halide to the reaction systems as a promotor give the nitrites, which are the intended reaction products, at relatively high yield. However, such processes are difficult of industrial practice because of the corrosion problem of the reaction equipments which incurs restrictions on the construction materials of the equipments. On the other hand, the processes not using any promotor give only low yield of nitrites and have not reached an industrially practiceable level.

DISCLOSURE OF THE INVENTION

Accordingly, therefore, the object of the present invention resides in provision of a process which is free of those defects in the conventional processes and which enables production of (meth)acrylonitriles at high yields and with industrial advantages.

We have made concentrative studies on production of (meth)acrylonitriles by ammoxidation process in which at least one saturated hydrocarbon selected from the group consisting of propane and isobutane is contacted with a mixed gas comprising molecular oxygen and ammonia in the vapor phase in the presence of a catalyst, to discover that meth(acrylonitrile) yields higher than those obtainable in conventional processes can be achieved by use of a catalyst composed of a complex oxide containing oxides of three elements of molybdenum, antimony and tungsten as the essential components, which is supported on a refractory inorganic carrier, and completed the present invention.

Thus, according to the invention a process is provided which comprises preparation of (meth)acrylonitriles by catalytically oxidizing propane and/or isobutane in the vapor phase, with molecular oxygen and ammonia in the presence of a catalyst, said process being characterized by use of a catalyst composed of a complex oxide which is expressed by the general formula (I) below:

$$Mo\alpha Sb\beta W\gamma Ox \qquad (I)$$

(in which α, β and γ denote the number of atoms of Mo, Sb and W, respectively, where, when α is 1, β is 0.5–10 and γ is 0.5–10; and x is a value determined by valence of the existing elements)

as supported on a refractory inorganic carrier.

Among the complex oxides expressed by above general formula (I), particularly those of the composition in which α is 1, β is 1 to 5 and γ is 1–5 give the intended nitriles at high yields.

It is furthermore preferred, according to the present invention, to use a catalyst composed of a complex oxide which contains, concurrently with the elements composing the complex oxide as expressed by above general formula (I), at least one element selected from the group consisting of Nb, Cr, Mn, Fe, Co and Ni (hereafter they may be referred to as "A group elements") in such an amount that the atomic ratio of A group element(s) to Mo exceeds 0 but not more than 0.5, as supported on a refractory inorganic carrier. These catalysts according to the present invention which additionally contain A group elements achieve the effect of improved activity or selectivity. Among the A group elements, Nb is particularly preferred for increasing yield of the object product. It is particularly preferred, furthermore, that the atomic ratio of A group element(s) to Mo is within a range of 0.05 to 0.2.

According to the invention, it is also preferred to use a catalyst composed of a complex oxide which contains, concurrently with the elements composing the complex oxide as expressed by general formula (I), at least one element selected from the group consisting of V, Nb, Cr, Mn, Fe, Co and Ni (hereafter they may be referred to as "A' group elements") in such an amount that the atomic ratio of the A' group element(s) to Mo exceeds 0 but not more than 0.5 and that of the A' group element(s) to the sum of Mo and W exceeds 0 but not more than 0.05, as supported on a refractory inorganic carrier. Among the A' group elements, V or Nb is particularly preferred for increasing yield of the object product. It is particularly preferred that the atomic ratio of the A' group element(s) to Mo is within a range of 0.05 to 0.2. Presence of the A' group element(s) is effective for improving activity or selectivity of the catalyst. The optimum content of the A' group element(s) depends on the composition of Mo and W. When the atomic ratio of the A' group element(s) to the sum of Mo and W exceeds the above limitative range, selectivity of the catalyst is adversely affected. Whereas, if the atomic ratio is less than the above range, little effect is achieved.

As the refractory inorganic carriers, silica, alumina, titania, zirconia, silica-alumina, silica-titania and silica-zirconia, etc. are preferred. Of those, use of alumina or silica-alumina is particularly preferred for improving yield of the object product.

Those catalysts useful for the present invention can be prepared by the methods known per se, which are routinely practiced in the technological field pertinent to the invention. For instance, they can be prepared by the steps of: dissolving ammonium paramolybdate in pure water under heating; adding thereto an aqueous solution of ammonium metatungstate; further adding antimony trioxide in powder form, and if necessary, an aqueous solution of at least one compound of at least one element selected from the group consisting of V, Nb, Cr, Mn, Fe, Co and Ni, and then a carrier such as silica, alumina and the like; mixing them by stirring for a predetermined length of time; heating and condensing the mixture; drying the resulting slurry; and then calcining the dried slurry at 400–800° C. The calcination can be conducted in open air, or in an atmosphere of high or low oxygen concentration. It is preferred to carry out the final calcination step in an atmosphere of low oxygen concentration (1%–15%), for obtaining high catalytic performance.

The materials to be used for preparing the catalyst useful for the invention are subject to no critical limitation, which may be, for example, nitrates, oxides, hydroxides, chlorides, carbonates, acetates, metallic acids, ammonium salts of metallic acids, etc. of the used elements.

As the starting materials of the carriers, besides shaped bodies of alumina, silica, silica-alumina, etc., powder, gel, sol, etc. of oxides or hydroxides can be suitably used in versatile ways according to the form of use of the catalyst.

As the material gases to be subjected to ammoxidation according to this invention, besides those of propane and/or isobutane, molecular oxygen and ammonia, diluent gases may be used if necessary. As the molecular oxygen source, air or pure oxygen can be used. Preferred molar ratio of molecular oxygen is 0.2–5 times by volume to propane, and that of ammonia is 0.2–3 times by volume to propane. As a diluent gas, an inert gas such as nitrogen, helium, carbon dioxide, etc., and steam or the like is conveniently used.

The vapor phase catalytic ammoxidation reaction according to the present invention can be conveniently practiced by contacting said material gases with said catalyst at a space velocity of 300–5,000 $hr^{-1}$ at a temperature between 300° C.–600° C. Said vapor phase catalytic ammoxidation is normally conducted under atmospheric pressure, but reduced or elevated pressures may be employed. The reaction system is subject to no critical limitation, but any of fixed bed, moving bed or fluidized bed systems can be adopted. Again, either single flow or recycling system is practiceable.

EFFECT OF THE INVENTION

According to the ammoxidation process of the present invention, at least one saturated hydrocarbon selected from the group consisting of propane and isobutane is catalytically oxidized by a mixed gas containing molecular oxygen and ammonia, in the presence of an above-described catalyst containing as the essential components molybdenum, antimony and tungsten, hereby (meth)acrylonitriles can be prepared at high yields with industrial advantages.

THE BEST EMBODIMENT FOR PRACTICING THE INVENTION

Hereinafter the present invention shall be explained still more specifically, referring to working examples.

In the following Examples, conversion, one pass yield and selectivity, inclusive of those of side products, are each defined as follows.

When the starting material is propane:

$$Conversion \text{ (mol \%)} = \frac{\text{mol } number\ of\ reacted\ propane}{\text{mol } number\ of\ fed\ propane} \times 100$$

$$Selectivity \text{ (mol \%)} = \frac{\frac{\text{mol } number\ of\ each\ of\ formed\ compounds}{\text{mol } number\ of\ reacted\ propane} \times \frac{carbon\ number\ of\ each\ compound}{3} \times 100$$

$$one\ pass\ yield \text{ (mol \%)} = \frac{\text{mol } number\ of\ each\ of\ formed\ compounds}{\text{mol } number\ of\ fed\ propane} \times \frac{carbon\ number\ of\ each\ compound}{3} \times 100$$

When the starting material is isobutane:

$$Conversion \text{ (mol \%)} = \frac{\text{mol } number\ of\ reacted\ isobutane}{\text{mol } number\ of\ fed\ isobutane} \times 100$$

$$Selectivity \text{ (mol \%)} = \frac{\frac{\text{mol } number\ of\ each\ of\ formed\ compounds}{\text{mol } number\ of\ reacted\ isobutane} \times \frac{carbon\ number\ of\ each\ compound}{4} \times 100$$

$$one\ pass\ yield \text{ (mol \%)} = \frac{\text{mol } number\ of\ each\ of\ formed\ compounds}{\text{mol } number\ of\ fed\ isobutane} \times \frac{carbon\ number\ of\ each\ compound}{4} \times 100$$

EXAMPLE 1

A 1 liter beaker was charged with 93.0 g of Alumina Sol A-200 (Nissan Chemical Industries; $Al_2O_3$ concentration: 10.5 wt %), 47.6 g of Silica Sol Snowtex N (Nissan Chemical Industries, $SiO_2$ concentration: 20.5 wt %) and 150 ml of water. The contents were stirred under heating, and maintained at about 80° C. Separately, 1.77 g of ammonium paramolybdate [$(NH_4)_6Mo_7O_{24} \cdot 4H_2O$: special grade reagent of Wako Junyaku] and 100 ml of water were put in a 300 ml beaker, stirred under heating and dissolved, and into which 13.91 g of an aqueous ammonium metatungstate [$(NH_4)_6H_2W_{12}O_{48}$] solution MW-2 (Nihon Muki-Kagaku Kogyo; containing 50 wt % of $WO_3$) was added. Further 4.38 g of $Sb_2O_3$ (Wako Junyaku, purity: 99.9%) as dispersed in 100 ml of water in a homogenizer was added, followed by 2 hours' stirring at about 80° C. for 2 hours, while maintaining the constant amount of the liquid. The resulting suspension was slowly added to the previously prepared alumina sol-silica sol mixed slurry dropwise. The system was stirred for further 2 hours at 80° C. while maintaining the constant amount of the liquid. The heating temperature was raised to 90° C. and stirring was continued to concentrate the system for about 4 hours, while allowing evaporation of its water content. The resulting paste was dried at 120° C. for 14 hours, and then calcined in open air at 450° C. for 3 hours. Calcination was further conducted in an atmosphere of oxygen concentration 10% (the balance was nitrogen), at 650° C. for 3 hours. Thus obtained catalyst had a composition of: 40 wt % $Mo_1Sb_3W_3Ox/30$ wt % $Al_2O_3$–30 wt % $SiO_2$ (here and in the subsequent identification of catalyst compositions, the left side of the slash/ shows composition of the complex oxide, and the right side, composition of the carrier).

This catalyst was dressed to 9–20 mesh size, and 5 ml thereof was filled in an ordinary flow reactor in which the reaction was conducted. The composition of the reaction gas was $C_3H_8/NH_3/O_2/He/H_2O=1/2/4/7.5/3$ (molar ratio), the space velocity SV employed was 900 hr$^{-1}$, and the reaction temperature was 580° C. The result of the reaction was as shown in Table 1.

EXAMPLE 2

The fed amounts of ammonium paramolybdate, aqueous ammonium metatungstate solution and $Sb_2O_3$ were changed to 1.13 g, 14.86 g and 4.67 g, respectively, and a catalyst was prepared by a process otherwise identical with the one employed in Example 1, which had a composition of 40 wt % $Mo_1Sb_5W_5Ox/30$ wt % $Al_2O_3$–30 wt % $SiO_2$. The reaction was carried out in the same manner as Example 1, except that the composition of the reaction gas was changed to $C_3H_8/NH_3/O_2/He=1/2/4/7.5$ (molar ratio) and the space velocity was changed to 750 hr$^{-1}$. The result was as shown in Table 1.

EXAMPLE 3

The fed amounts of ammonium paramolybdate, aqueous ammonium metatungstate solution and $Sb_2O_3$ were changed to 3.59 g, 5.79 9 and 3.64 9, respectively, and a catalyst was prepared by a process otherwise identical with the one employed in Example 1, which had a composition of 40 wt % $Mo_1Sb_1W_1Ox/30$ wt % $Al_2O_3$–30 wt % $SiO_2$. The reaction was carried out in the same manner as Example 1, except that the reaction temperature was changed to 540° C. The result was as shown in Table 1.

EXAMPLE 4

A catalyst was prepared by a process identical with the one employed in Example 1, except that 0.175 g of ammonium metavanadate ($NH_4VO_3$, special grade reagent manufactured by Wako Junyaku) as dissolved in 30 ml of water under heating was added after addition of the aqueous ammonium metatungstate solution and before addition of $Sb_2O_3$ dispersion. The resulting catalyst had a composition of 40 wt % $Mo_1Sb_3W_3V_{0.15}Ox/30$ wt % $Al_2O_3$–30 wt % $SiO_2$. The reaction was carried out in the identical manner with Example 1, except that the reaction temperature was changed to 560° C. The result was as shown in Table 1.

EXAMPLE 5

A catalyst was prepared by a process identical with the one employed in Example 4 except that the used amounts of ammonium paramolybdate, aqueous ammonium metatungstate solution, ammonium metavanadate and $Sb_2O_3$ were changed to 1.38 g, 14.45 g, 0.164 g and 4.54 g, respectively. Thus, a catalyst having a composition of 40 wt % $Mo_1Sb_4W_4V_{0.18}Ox/30$ wt % $Al_2O_3$–30 wt % $SiO_2$ was obtained. The reaction was carried out in the identical manner with Example 1, except that the composition of the reaction gas was changed to $C_3H_8/NH_3/O_2/He=1/2/4/7.5$ (molar ratio), the space velocity was changed to 750 hr$^-$ and the reaction temperature was changed to 560° C. The result was as shown in Table 1.

EXAMPLE 6

A catalyst was prepared in identical manner with Example 4, except that an aqueous solution of 0.972 g of niobium oxalate (made by CBMM, containing 20.5 wt % as $Nb_2O_5$) as dissolved in 100 ml of warm water was added instead of the aqueous ammonium metavanadate solution.

The catalyst had a composition of 40 wt % $Mo_1Sb_3W_3Nb_{0.15}Ox/30$ wt % $Al_2O_3$–30 wt % $SiO_2$. The reaction was carried out in the identical manner with Example 1, except that the reaction temperature was changed to 570° C. The result was as shown in Table 1.

EXAMPLE 7

A catalyst was prepared by a process identical with the one employed in Example 4, except that an aqueous solution of 0.600 g of chromium nitrate $[Cr(NO_3)_3.9H_2O$, a reagent manufactured by Wako Junyaku, purity: 99.9%] as dissolved in 100 ml of warm water was added instead of the aqueous ammonium metavanadate solution. The catalyst obtained had a composition of 40 wt % $Mo_1Sb_3W_3Cr_{0.15}Ox/30$ wt % $Al_2O_3$–30 wt % $SiO_2$. The reaction was carried out in the identical manner with Example 1. The result was as shown in Table 1.

EXAMPLE 8

A catalyst was prepared in the identical manner with Example 4, except that the aqueous ammonium metavanadate solution was replaced by an aqueous solution of 0.436 g of nickel nitrate $[Ni(NO_3)_2.6H_2O$, a special grade reagent manufactured by Wako Junyaku] as dissolved in 100 ml of warm water. The resulting catalyst had a composition of 40 wt % $Mo_1Sb_3W_3Ni_{0.15}Ox/30$ wt % $Al_2O_3$–30 wt % $SiO_2$. The reaction was conducted in the manner identical with Example 1 except that the reaction temperature was changed to 570° C. The result was as shown in Table 1.

EXAMPLE 9

A catalyst was prepared in the manner identical with Example 4, except that the aqueous ammonium metavanadate solution was replaced by 0.431 g of manganese nitrate $[Mn(NO_3)_2.6H_2O$, a special grade reagent manufactured by Wako Junyaku] as dissolved in 100 ml of warm water. The catalyst had a composition of 40 wt % $Mo_1Sb_3W_3Mn_{0.15}Ox/30$ wt % $Al_2O_3$–30 wt % $SiO_2$. The reaction was carried out in the identical manner with Example 1, except that the reaction temperature was changed to 570° C. The result obtained was as shown in Table 1.

EXAMPLE 10

A catalyst was prepared in the manner identical with Example 1 except that Silica Sol Snowtex N was not used. The catalyst had a composition of 57 wt % $Mo_1Sb_3W_3Ox/43$ wt % $Al_2O_3$. The reaction was carried out in the manner identical with Example 1. The result was as shown in Table 1.

COMPARATIVE EXAMPLE 1

A catalyst was prepared in the manner identical with Example 1, except that no ammonium metatungstate was used and that the fed amounts of ammonium paramolybdate and $Sb_2O_3$ were changed to 3.80 g and 9.40 g, respectively. The catalyst had a composition of 40 wt % $Mo_1Sb_3Ox/30$ wt % $Al_2O_3$–30 wt % $SiO_2$. The reaction was carried out in the manner identical with Example 1. The result was as shown in Table 2.

COMPARATIVE EXAMPLE 2

A catalyst was prepared in the manner identical with Example 1, except that no $Sb_2O_3$ was used and that the fed amounts of ammonium paramolybdate and the aqueous ammonium metatungstate solution MW-2 were changed to 2.74 g and 21.55 g, respectively. The catalyst had a composition of 40 wt % $Mo_1W_3Ox/30$ wt % $Al_2O_3$–30 wt % $SiO_2$. The reaction was carried out in the identical manner with Example 1, except that the reaction temperature was changed to 520° C. The result was as shown in Table 2.

COMPARATIVE EXAMPLE 3

A catalyst was prepared in the manner identical with Example 1, except that no ammonium paramolybdate was used and that the fed amounts of the aqueous ammonium metatungstate solution MW-2 and $Sb_2O_3$ were changed to 15.64 g and 4.92 g, respectively. The catalyst had a composition of 40 wt % $Sb_1W_1Ox/30$ wt % $Al_2O_3$–30 wt % $SiO_2$. The reaction was carried out in the manner identical with Example 1. The result was as shown in Table 2.

COMPARATIVE EXAMPLE 4

A catalyst was prepared in the manner identical with Example 1, except that the fed amounts of ammonium paramolybdate, the aqueous ammonium metatungstate solution and $Sb_2O_3$ were changed to 0.88 g, 5.99 g and 9.42g, respectively. The catalyst had a composition of 40 wt % $Mo_1Sb_{15}W_3Ox/30$ wt % $Al_2O_3$–30 wt % $SiO_2$. The reaction was carried out in the manner identical with Example 1. The result was as shown in Table 2.

COMPARATIVE EXAMPLE 5

A catalyst was prepared in the manner identical with Example 1, except that the fed amounts of ammonium paramolybdate, the aqueous ammonium metatungstate solution and $Sb_2O_3$ were changed to 0.57 g, 22.3 g and 1.40 g, respectively. The catalyst had a composition of 40 wt % $Mo_1Sb_3W_{15}Ox/30$ wt % $Al_2O_3$–30 wt % $SiO_2$. The reaction was carried out in the manner identical with Example 1. The result was as shown in Table 2.

COMPARATIVE EXAMPLE 6

A catalyst was prepared in the manner identical with Example 4, except that the fed amount of the ammonium metavanadate was changed to 0.702 g. The catalyst had a composition of 41 wt % $Mo_1Sb_3W_3V_{0.6}Ox/29.5$ wt % $Al_2O_3$–29.5 wt % $SiO_2$. The reaction was carried out in the manner identical with Example 1 except that the reaction temperature was changed to 540° C. The result was as shown in Table 2.

EXAMPLE 11

The reaction was carried out using the same catalyst as the one used in Example 4. The composition of the reaction gas was i-$C_4H_{10}$/$NH_3$/$O_2$/He/$H_2O$=1/2/4/7.5/3 (molar ratio), the space velocity was 900 hr$^{-1}$, and the reaction temperature was 520° C. Consequently, isobutane conversion of 69.0%, selectivity for methacrylonitrile of 46.8% and one pass yield of methacrylonitrile of 32.3% were obtained.

TABLE 1

| Example No. | Catalyst Composition[1] | Gas[2] Composition | Reaction Temp. (° C.) | Propane Conversion (%) | Selectivity (%) AN[3] | Selectivity (%) $C_3'$[4] | Selectivity (%) HCN[5] | One pass yield (%) AN[3] | One pass yield (%) AN + $C_3'$[6] |
|---|---|---|---|---|---|---|---|---|---|
| 1 | 40 wt. % $Mo_1Sb_3W_3Ox$ | A | 580 | 70.1 | 50.2 | 11.9 | 8.5 | 35.2 | 43.5 |
| 2 | 40 wt. % $Mo_1Sb_5W_3Ox$ | B | 580 | 67.8 | 43.9 | 3.7 | 8.4 | 29.8 | 32.3 |
| 3 | 40 wt. % $Mo_1Sb_1W_1Ox$ | A | 540 | 72.3 | 40.1 | 9.8 | 7.3 | 29.0 | 36.1 |
| 4 | 40 wt. % $Mo_1Sb_3W_3V_{0.15}Ox$ | A | 560 | 73.0 | 56.1 | 10.2 | 9.3 | 41.0 | 48.4 |
| 5 | 40 wt. % $Mo_1Sb_4W_4V_{0.18}Ox$ | B | 560 | 82.2 | 50.9 | 5.1 | 8.8 | 41.8 | 46.0 |
| 6 | 40 wt. % $Mo_1Sb_3W_3Nb_{0.15}Ox$ | A | 570 | 71.2 | 52.8 | 11.3 | 8.7 | 37.6 | 45.6 |
| 7 | 40 wt. % $Mo_1Sb_3W_3Cr_{0.15}Ox$ | A | 580 | 73.5 | 48.4 | 12.0 | 9.6 | 35.6 | 44.4 |
| 8 | 40 wt. % $Mo_1Sb_3W_3Ni_{0.15}Ox$ | A | 570 | 68.9 | 52.1 | 11.4 | 8.3 | 35.9 | 43.8 |
| 9 | 40 wt. % $Mo_1Sb_3W_3Mn_{0.15}Ox$ | A | 570 | 71.8 | 49.8 | 11.7 | 8.9 | 35.8 | 44.2 |
| 10 | 57 wt. % $Mo_1Sb_3W_3Ox$ | A | 580 | 76.3 | 37.4 | 6.2 | 9.3 | 28.5 | 33.3 |

[1]As the carrier, $Al_2O_3$:$SiO_2$ = 1:1 (by weight) was used in Examples 1–9, and $Al_2O_3$ was used in Example 10.
[2]Gas composition A: $C_3H_8$/$NH_3$/$O_2$/He/$H_2O$ = 1/2/4/7.5/3 (molar ratio)
Gas composition B: $C_3H_8$/$NH_3$/$O_2$/He = 1/2/4/7.5 (molar ratio)
[3]AN: acrylonitrile
[4]$C_3'$: propylene
[5]HCN: hydrogen cyanide
[6]AN + $C_3'$: sum of acrylonitrile and propylene

TABLE 2

| Comparative Example No. | Catalyst Composition[1] | Gas[2] Composition | Reaction Temp. (° C.) | Propane Conversion (%) | Selectivity (%) AN[3] | Selectivity (%) $C_3'$[4] | Selectivity (%) HCN[5] | One pass yield (%) AN[3] | One pass yield (%) AN + $C_3'$[6] |
|---|---|---|---|---|---|---|---|---|---|
| 1 | 40 wt. % $Mo_1Sb_3Ox$ | A | 580 | 52.0 | 30.1 | 14.7 | 5.9 | 15.7 | 23.3 |
| 2 | 40 wt. % $Mo_1W_3Ox$ | A | 520 | 65.0 | 12.1 | 6.9 | 2.6 | 7.9 | 12.4 |
| 3 | 40 wt. % $Sb_1W_3Ox$ | A | 580 | 38.4 | 20.7 | 29.2 | 3.3 | 7.9 | 19.2 |
| 4 | 40 wt. % $Mo_1Sb_{15}W_3Ox$ | A | 580 | 28.9 | 13.6 | 32.1 | 7.5 | 3.9 | 13.2 |
| 5 | 40 wt. % $Mo_1Sb_3W_{15}Ox$ | A | 580 | 49.1 | 10.8 | 21.0 | 2.9 | 4.9 | 15.6 |
| 6 | 41 wt. % $Mo_1Sb_3W_3V_{0.6}Ox$ | A | 540 | 68.7 | 28.2 | 14.1 | 5.9 | 19.4 | 29.1 |

[1]As the carrier, $Al_2O_3$:$SiO_2$ = 1:1 (by weight) was used in all of the Comparative Examples.
[2]Gas composition A: $C_3H_8$/$NH_3$/$O_2$/He/$H_2O$ = 1/2/4/7.5/3 (molar ratio)
[3]AN: acrylonitrile
[4]$C_3'$: propylene
[5]HCN: hydrogen cyanide
[6]AN + $C_3'$: sum of acrylonitrile and propylene

We claim:

1. A process for the preparation of (meth)acrylonitriles by an ammoxidation process in which at least one saturated hydrocarbon selected from the group consisting of propane and isobutane is catalytically oxidized with a mixed gas containing molecular oxygen and ammonia in the presence of a catalyst, wherein the catalyst composed of complex oxide expressed by the general formula (I) below:

$$Mo_\alpha Sb_\beta W_\gamma O_x \tag{I}$$

(in which $\alpha$, $\beta$ and $\gamma$ denote the number of atoms of Mo, Sb and W, respectively, and when $\alpha$ is 1, $\beta$ is 0.5–10 and $\gamma$ is 0.5–10; and x is a value determined by valence of the existing elements)
as supported on a refractory inorganic carrier.

2. The process as described in claim 1, wherein the catalyst which contains, concurrently with the constituent elements of the complex oxide as expressed by the general formula (I), at least one element selected from the group consisting of Nb, Cr, Mn, Fe, Co and Ni, in such an amount that the atomic ratio of the selected element or elements to Mo exceeds 0 but is not more than 0.5.

3. The process as described in claim 1, wherein the catalyst which contains, concurrently with the constituent elements of the complex oxide as expressed by the general formula (I), at least one element selected from the group consisting of V, Nb, Cr, Mn, Fe, Co and Ni, in such an amount that the atomic ratio of the selected element or elements to Mo exceeds 0 but is not more than 0.5 and said ratio to the sum of Mo and W exceeds 0 but is not more than 0.05.

4. A catalyst for preparing (meth)acrylonitriles through ammoxidation of at least one saturated hydrocarbon selected from the group consisting of propane and isobutane, which is composed of complex oxide expressed by the general formula (I) below:

$$Mo_\alpha Sb_\beta W_\gamma O_x \tag{I}$$

(in which $\alpha$, $\beta$ and $\gamma$ denote the number of atoms of Mo, Sb and W, respectively, and when $\alpha$ is 1, $\beta$ is 0.5–10 and $\gamma$ is 0.5–10; and x is a value determined by valence of the existing elements)
as supported on a refractory inorganic carrier.

5. A catalyst as described in claim 4 which contains, concurrently with the constituent elements of the complex oxide expressed by the general formula (I) as set forth in claim 4, at least one element selected from the group consisting of Nb, Cr, Mn, Fe, Co and Ni, in such an amount that the atomic ratio of the selected element or elements to Mo exceeds 0 but is not more than 0.5.

6. A catalyst as described in claim 4 which contains, concurrently with the constituent elements of the complex oxide expressed by the general formula (I) as set forth in claim 4, at least one element selected from the group consisting of V, Nb, Cr, Mn, Fe, Co and Ni, in such an amount that the atomic ratio of the selected element or elements to Mo exceeds 0 but is not more than 0.5 and that of the selected element or elements to the sum of Mo and W exceeds 0 but is not more than 0.05.

* * * * *